(12) United States Patent
Framroze

(10) Patent No.: US 8,669,371 B2
(45) Date of Patent: Mar. 11, 2014

(54) REGIOSELECTIVE CHLORINATION OF THE PHENYL RING OF 4,5-DIHYDRO-1-PHENYL-1H-1,2,4-TRIAZOL-5-ONES

(76) Inventor: Bomi Patel Framroze, Cambridge, MA (US)

( * ) Notice: Subject to any disclaimer, the term of this patent is extended or adjusted under 35 U.S.C. 154(b) by 0 days.

(21) Appl. No.: 13/584,098

(22) Filed: Aug. 13, 2012

(65) Prior Publication Data

US 2013/0072689 A1   Mar. 21, 2013

Related U.S. Application Data

(60) Provisional application No. 61/537,477, filed on Sep. 21, 2011.

(51) Int. Cl.
*C07D 249/12* (2006.01)
(52) U.S. Cl.
CPC .................... *C07D 249/12* (2013.01)
USPC ....................................... 548/263.2
(58) Field of Classification Search
USPC ...................................... 548/263.2
See application file for complete search history.

(56) References Cited

U.S. PATENT DOCUMENTS 4,980,480 A    12/1990   Theodoridis
5,468,868 A *  11/1995   Halfon et al. ............. 548/263.2

OTHER PUBLICATIONS

Seguchi, et al., Bull. Chem. Soc. Jap., 43(10), 1970, pp. 3318.*
Bull. Chem. Soc. Jap. 43 (10), 3318, (1970), Seguchi et al.
J. Am. Chem. Soc. 74, 3171, (1952), Adams & Braun.

* cited by examiner

*Primary Examiner* — Michael Barker
(74) *Attorney, Agent, or Firm* — David M. Gange

(57) ABSTRACT

An improved process for selectively chlorinating 4,5-dihydro-1-phenyl-1H-1,2,4-triazole-5-ones, including 4,5-dihydro-3-alkyl-1-phenyl-1H-1,2,4-triazole-5-ones and 4-haloalkyl-4, 5-dihydro-3-alkyl-1-phenyl-1H-1,2,4-triazole-5-ones in the 4-position of the phenyl ring by dissolving the compounds in a synergistic ratio of polar aprotic solvents, preferably acetonitrile and N,N-dimethylformamide in a 7:3 ratio and reacting the solution with chlorine gas.

10 Claims, No Drawings

REGIOSELECTIVE CHLORINATION OF THE PHENYL RING OF 4,5-DIHYDRO-1-PHENYL-1H-1,2,4-TRIAZOL-5-ONES

CROSS REFERENCE TO RELATED APPLICATIONS

This application claims the benefit of U.S. Provisional Application Ser. No. 61/537,477, filed Sep. 21, 2011. This application is hereby included herein by reference in its entirety.

FIELD

This invention relates to a process for regioselectively chlorinating 4,5-dihydro-3-alkyl-1-phenyl-1H-1,2,4-triazole-5-one and 4-haloalkyl-4,5-dihydro-3-alkyl-1-phenyl-1H-1,2,4-triazole-5-one in the 4-position of the phenyl ring by dissolving the compounds in a synergistic ratio of a mixture of polar aprotic solvents followed by reaction with chlorine gas.

BACKGROUND

Regioselective chlorination of substituted phenyl rings is a desirable process step for the manufacture of many agrochemical and pharmaceutical products. Regioselective phenyl chlorination of 4,5-dihydro-1-phenyl-1H-1,2,4-triazole-5-ones in the 4-position is desirous for the synthesis of certain agrochemicals such as herbicides and insecticides. U.S. Pat. No. 4,980,480 describes numerous methods to prepare 4-halogenated phenyltriazole-5-ones but does not describe any specific use of reagents or solvents. U.S. Pat. No. 5,468,868 more specifically describes a two step sequence of chlorinations to first regioselectively introduce the 4-chloro group followed by the 2-chloro group in triazole-5-one compounds. The authors proceed to show that N,N-dimethylformamide (DMF) is the best solvent for the first step of 4-chloro substitution, showing the highest selectivity and yield. The authors further show that acetonitrile, although a cheaper and easier handled solvent, is not able to achieve the 90%+ regioselectivity for the 4-position, as required for intermediates of this kind to be commercially useful.

Further, nowhere in U.S. Pat No. 5,468,868 do these authors describe the potential use of mixed polar solvents leading to the preferred regioselective chlorination on the 4-position of the phenyl ring in a unpredictable ratio.

The literature also contains some reports of chlorination of phenyl rings in polar solvents such as N,N-dimethylformamide and acetonitrile. For example, R Adams et al in J. Am. Chem. Soc. 74, 3171, (1952) describes the chlorination of a benzenesulfonamide in DMF as the solvent. In another reference, Bull. Chem. Soc. Jap. 43 (10), 3318, (1970) the authors describe chiorinations in DMF or acetonitrile in which the ortho/para ratio is directly proportional to the dielectric constant of the solvent used.

This result is in direct contrast to the unexpected synergy observed when mixed solvents of high dielectric constant are added together in the certain ratios an herein described in this application.

Further, all of the references teach that DMF is the preferred solvent of choice for chlorinations of the 4-position of the phenyl ring in 4,5-dihydro-1-phenyl-1H-1,2,4-triazol-5-ones, which is in direct contrast to the results described and claimed herein, where increasing the DMF ratio past 50:50 with acetonitrile leads to a loss in regioselectivity, with 70:30 being the most preferred ratio of acetonitrile:DMF. Acetonitrile is less expensive than DMF and is easier to use and recover on a large scale. The mixed solvent described herein allows for a more commercially viable process with the desired enhanced regioselectivity that has not been described or inferred previously in the prior art.

The patents described above, and all patents discussed in this application, are hereby incorporated herein by reference in their entirety.

SUMMARY

This invention relates to a process for selectively chlorinating 4,5-dihydro-1-phenyl-1H-1,2,4-triazole-5-ones, including 4,5-dihydro-3-alkyl-1-phenyl-1H-1,2,4-triazole-5-ones and 4-haloalkyl-4,5-dihydro-3-alkyl-1-phenyl-1H-1,2,4-triazole-5-ones in the 4-position of the phenyl ring by dissolving the compounds in a synergistic ratio of polar aprotic solvents and reacting the same with chlorine gas. The preferred polar aprotic solvents used are acetonitrile and DMF in a ratio of 50:50 to 70:30 respectively, which improves the regioselectively for chlorination at the 4-position over the 2-position of the phenyl ring, over that achieved by the acetonitrile by itself.

DETAILED DESCRIPTION

Before describing the present invention in detail, it is to be understood that the terminology used herein is for the purpose of describing particular embodiments only, and is not intended to be limiting.

In accordance with the present invention, there is provided a process to produce, in a highly regioselective manner, the agrochemically and pharmaceutically important intermediates 1-(4-chlorophenyl)-4,5-dihydro-3-methyl-1H-1,2,4-triazole-5-one and 1-(4-chlorophenyl)-4-difluoromethyl-4,5-dihydro-3-methyl-1-phenyl-1H-1,2,4-triazole-5-one.

Thus, the method according to the present invention can be carried out with any 4,5-dihydro-3-alkyl-1-phenyl-1H-1,2,4-triazole-5-one and 4-haloalkyl-4,5-dihydro-3-alkyl-1-phenyl-1H-1,2,4-triazole-5-one being chlorinated in a mixture of 50:50 to 70:30 acetonitrile:DMF with chlorine gas to yield 90%+ of the 1-(4-chlorophenyl) products. It will be clear to those skilled in the art that modifications can be made to the process described herein without departing from the inventive concept set forth in our claims below.

Example 1: Preparation of 1-(4-chlorophenyl)-4,5-dihydro-3-methyl-5-one in 100% DMF solvent In a two neck 250 ml flask equipped with a magnetic stir bar, dip tube and dry ice condenser was added 20 grams of 4,5-dihydro-3-methyl-1-phenyl-1H-1,2,4-triazole-5-one and 200 ml of DMF and the reaction cooled to 0° C. 1.5 equivalents of chlorine gas was bubbled into the reaction mixture for 30 minutes while allowing the reaction temperature to rise to 15° C. Gas chromatographic analysis of the reaction mixture with an internal standard calibration showed a 92% yield and 93% regioselectivity for the 1-(4-chlorophenyl)-4,5-dihydro-3-methyl-1H-1,2,4-triazole-5-one.

Example 2: Preparation of 1-(4-chlorophenyl)-4,5-dihydro-3-methyl-1H-1,2,4-triazole-5-one in 100% acetonitrile solvent In a two neck 250 ml flask equipped with a magnetic stir bar, dip tube and dry ice condenser was added 20 grams of 4,5-dihydro-3-methyl-1-phenyl-1H-1,2,4-triazole-5-one and 200 ml of acetonitrile and the reaction cooled to 0° C. 1.5 equivalents of chlorine gas was bubbled into the reaction mixture for 40 minutes while allowing the reaction temperature to rise to 15° C. Gas chromatographic analysis of the reaction mixture with an internal standard calibration showed a 85% yield and 84% regioselectivity for the 1-(4-chlorophenyl)-4,5-dihydro-3-methyl-1H-1,2,4-triazole-5-one.

Example 3: Preparation of 1-(4-chlorophenyl)-4,5-dihydro-3-methyl-1H-1,2,4-5-one in 50% acetonitrile:50% DMF solvent In a two neck 250 ml flask equipped with a magnetic stir bar, dip tube and dry ice condenser was added 20 grams of 4,5-dihydro-3-methyl-1-phenyl-1H-1,2,4-triazole-5-one and 200 ml of a 1:1 mixture of acetonitrile and DMF and the reaction cooled to 0° C. 1.5 equivalents of chlorine gas was bubbled into the reaction mixture for 30 minutes while allowing the reaction temperature to rise to 15° C. Gas chromatographic analysis of the reaction mixture with an internal standard calibration showed a 91% yield and 92% regioselectivity for the 1-(4-chlorophenyl)-4,5-dihydro-3-methyl-1H-1,2,4-triazole-5-one.

Example 4: Preparation of 1-(4-chlorophenyl)-4,5-dihydro-3-methyl-1H-1,2,4-triazole-5-one in 70% acetonitrile:30% DMF solvent In a two neck 250 ml flask equipped with a magnetic stir bar, dip tube and dry ice condenser was added 20 grams of 4,5-dihydro-3-methyl-1-phenyl-1H-1,2,4-triazole-5-one and 200 ml of a 7:3 mixture of acetonitrile and DMF and the reaction cooled to 0° C. 1.5 equivalents of chlorine gas was bubbled into the reaction mixture for 30 minutes while allowing the reaction temperature to rise to 15° C. Gas chromatographic analysis of the reaction mixture with an internal standard calibration showed a 92% yield and 95% regioselectivity for the 1-(4-chlorophenyl)-4,5-dihydro-3-methyl-1H-1,2,4-triazole-5-one.

Example 5: Preparation of 1-(4-chlorophenyl)-4,5-dihydro-3-methyl-1H-1,2,4-triazole-5-one in 30% acetonitrile:70% DMF solvent In a two neck 250 ml flask equipped with a magnetic stir bar, dip tube and dry ice condenser was added 20 grams of 4,5-dihydro-3-methyl-1-phenyl-1H-1,2,4-triazole-5-one and 200 ml of a 3:7 mixture of acetonitrile and DMF and the reaction cooled to 0° C. 1.5 equivalents of chlorine gas was bubbled into the reaction mixture for 30 minutes while allowing the reaction temperature to rise to 15° C. Gas chromatographic analysis of the reaction mixture with an internal standard calibration showed a 88% yield and 84% regioselectivity for the 1-(4-chlorophenyl)-4,5-dihydro-3-methyl-1H-1,2,4-triazole-5-one.

Example 6: Preparation of 1-(4-chlorophenyl)-4-difluoromethyl-4,5-dihydro-3-methyl-1H-1,2,4-triazole-5-one in 70% acetonitrile:30% DMF solvent In a two neck 250 ml flask equipped with a magnetic stir bar, dip tube and dry ice condenser was added 20 grams of 4-difluoromethyl-4,5-dihydro-3-methyl-1-phenyl-1H-1,2,4-triazole-5-one and 200 ml of a 7:3 mixture of acetonitrile and DMF and the reaction cooled to 0° C. 1.5 equivalents of chlorine gas was bubbled into the reaction mixture for 30 minutes while allowing the reaction temperature to rise to 15° C. Gas chromatographic analysis of the reaction mixture with an internal standard calibration showed a 92% yield and 94% regioselectivity for the 1-(4-chlorophenyl)-4-difluoromethyl-4,5-dihydro-3-methyl-1H-1,2,4-triazole-5-one.

Example 7: General Procedure for the preparation of 4,5-dihydro-1-phenyl-1H-1,2,4-triazol-5-ones Into a reaction vessel equipped with stirring, dip tube, and condenser add 1 equivalent of a 4,5-dihydro-1-phenyl-1H-1,2,4-triazol-5-one and a 70:30 mixture of acetonitrile and DMF in sufficient quantity to dissolve the 4,5-dihydro-1-phenyl-1H-1,2,4-triazol-5-one. Cool the mixture to between −10° C. and +10° C. Bubble 1.5 equivalents of chlorine gas into the reaction mixture for 30 minutes while allowing the reaction temperature to rise to 15° C. Remove the solvent via evaporation under vacuum and isolate the product.

What is claimed is:

1. A process for the selective chlorination of a 4,5-dihydro-1-phenyl-1H-1,2,4-triazole-5-one in the 4-position of the phenyl ring;
    where the 4,5-dihydro-1-phenyl-1H-1,2,4-triazole-5-one is selected from the group consisting of 4,5-dihydro-3-methyl-1-phenyl-1H-1,2,4-triazole-5-one and 4-difluoromethyl-4,5-dihydro-3-methyl-1-phenyl-1H-1,2,4-triazole-5-one;
    which comprises the steps of:
    a) charging a reaction vessel with a polar aprotic solvent mixture and a 4,5-dihydro-1-phenyl-1H-1,2,4-triazole-5-one;
    b) cooling the 4,5-dihydro-1-phenyl-1H-1,2,4-triazole-5-one and solvent mixture to 0° C.;
    c) adding 1.5 equivalents of chlorine gas to the mixture over a period of 30 minutes while allowing the temperature to warm to 15° C.

2. A process according to claim 1, wherein the solvent mixture is comprised of acetonitrile and N,N-dimethylformamide.

3. A process according to claim 1, wherein the ratio of acetonitrile and DMF is between about 1:1 and 3:1.

4. A process according to claim 3, wherein the most preferred ratio of acetonitrile and DMF is about 7:3.

5. A process according to claim 1 wherein the temperature of the reaction is between −10° C. and +10° C. at the beginning of the chlorine gas addition.

6. A process for the selective chlorination of a 4,5-dihydro-1-phenyl-1H-1,2,4-triazole-5-one in the 4-position of the phenyl ring;
    which comprises the steps of:
    a) charging a reaction vessel with a polar aprotic solvent mixture and a 4,5-dihydro-1-phenyl-1H-1,2,4-triazole-5-one;
    b) cooling the 4,5-dihydro-1-phenyl-1H-1,2,4--triazole-5-one and solvent mixture to 0° C.;
    c) adding 1.5 equivalents of chlorine gas to the mixture over a period of 30 minutes while allowing the temperature to warm to 15° C.

7. A process according to claim 6, wherein the solvent mixture is comprised of acetonitrile and N,N-dimethylformamide.

8. A process according to claim 6, wherein the ratio of acetonitrile and DMF is between about 1:1 and 3:1.

9. A process according to claim 8, wherein the most preferred ratio of acetonitrile and DMF is about 7:3.

10. A process according to claim 6 wherein the temperature of the reaction is between −10° C. and +10° C. at the beginning of the chlorine gas addition.

* * * * *